United States Patent
Oku et al.

(10) Patent No.: US 7,813,794 B2
(45) Date of Patent: Oct. 12, 2010

(54) BODY FAT MEASURING APPARATUS CAPABLE OF MEASURING VISCERAL FAT WITH HIGH ACCURACY

(75) Inventors: Shojiro Oku, Kyoto (JP); Toshikazu Shiga, Otsu (JP); Yoshitake Oshima, Kyoto (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 22 days.

(21) Appl. No.: 11/390,278

(22) Filed: Mar. 28, 2006

(65) Prior Publication Data

US 2006/0224080 A1   Oct. 5, 2006

(30) Foreign Application Priority Data

Mar. 30, 2005   (JP)   .............................. 2005-096686

(51) Int. Cl.
    A61B 5/05   (2006.01)
(52) U.S. Cl. .................................................... 600/547
(58) Field of Classification Search ................ 600/547, 600/536, 506, 300; 606/32, 34
    See application file for complete search history.

(56) References Cited

U.S. PATENT DOCUMENTS

| | | | |
|---|---|---|---|
| 5,335,667 A * | 8/1994 | Cha et al. .................... | 600/547 |
| 7,203,536 B2 * | 4/2007 | Masuo ........................ | 600/547 |
| 2004/0054298 A1 | 3/2004 | Masuo et al. | |
| 2004/0077969 A1* | 4/2004 | Onda et al. ................. | 600/547 |
| 2004/0236245 A1* | 11/2004 | Shiokawa .................... | 600/547 |

FOREIGN PATENT DOCUMENTS

| | | |
|---|---|---|
| EP | 1554976 | 7/2005 |
| JP | 2001-252257 | 9/2001 |
| JP | 2002-369806 | 12/2002 |
| WO | WO-02/24069 | 3/2002 |
| WO | WO-03/105688 | 12/2003 |
| WO | WO2006080345 A1 * | 8/2006 |

OTHER PUBLICATIONS

Ryo et al. (2003) "Development Of Method For Measuring Visceral Fat With Abdominal Impedance Analysis", Study of Obesity 9(2), pp. 32-38.
European Office Action dated Jan. 15, 2008, directed to counterpart foreign Application No. 06 006 155.3-1526.

* cited by examiner

*Primary Examiner*—Max Hindenburg
*Assistant Examiner*—Fangemonique Smith
(74) *Attorney, Agent, or Firm*—Morrison & Foerster LLP (57) ABSTRACT

In a body fat measuring apparatus, a constant electric-current is flowed between hand electric-current electrodes and leg electric-current electrodes. From two detected voltages generated between an annular-shaped voltage electrode placed on an abdominal portion and two voltage electrodes placed at the both sides of a lumbar portion, two abdominal impedances are determined. Two electric-current electrodes and two voltage electrodes are placed such that they are spaced apart by a small interval from one another at an umbilicus portion. A constant electric current is flowed between the two electric-current electrodes and the impedance in the vicinity of the subcutaneous of the abdominal portion is determined from the detected voltage generated between the two voltage electrodes. From the two abdominal impedances, the impedance in the vicinity of the subcutaneous of the abdominal portion, and the input physique information, a viscera impedance is calculated.

8 Claims, 8 Drawing Sheets

BODY FAT MEASURING APPARATUS CAPABLE OF MEASURING VISCERAL FAT WITH HIGH ACCURACY

BACKGROUND OF THE INVENTION

1. Field of the Invention

The present invention relates to a body fat measuring apparatus, in particular, a body fat measuring apparatus capable of measuring visceral fat with high accuracy.

2. Description of the Background Art

As a method for measuring visceral fat, in recent years, there has been known a method for capturing an abdominal cross-sectional image using an X-ray CT, an MRI and the like and determining an area of a fat region occupying the cross-sectional image. Further, as another method, there has been disclosed a method which places a pair of electric-current electrodes on a back portion and an umbilical portion of an abdominal portion, places a pair of detection voltage electrodes on both flank portions, determines a bioelectrical impedance of the abdominal portion from the detected voltage between the voltage electrodes during energization between the electric-current electrodes and determines visceral fat from the bioelectrical impedance (refer to, for example, Japanese Patent Laying-Open Nos. 2001-252257 and 2002-369806, and a literature "Development of Visceral-Fat Measuring Method by Abdominal Bioelectrical Impedance Method", Study of Obesity, Vol. 9, No. 2, 2003). Further, as a bioelectrical-fat measuring method using a bioelectrical impedance analysis, there has been disclosed a method which places electric-current electrodes on four limbs, energizes between the electric-current electrodes, places a pair of voltage electrodes at arbitrary two points between the electric-current electrodes provided on the four limbs and determines the impedance between the arbitrary two points (refer to, for example, U.S. Pat. No. 5,335,667).

Out of the aforementioned visceral-fat measuring methods, the method using an abdominal cross-sectional image taken through an X-ray CT or an MRI has a problem that it involves a large-size apparatus and therefore measurements of visceral fat can be performed only in medical institutions equipped with such facilities and can not be readily conducted everywhere.

Further the visceral fat measuring methods disclosed in the aforementioned two publications and the aforementioned literature are predicated on the fact that visceral fat exists as a lump at the center of the abdominal portion, as a measurement principle. However, visceral fat is stuck on the mesenterium in an actual human body and is distributed to some degrees, rather than exists as a lump. Therefore, these methods have the problem of inaccuracy of measurements.

Furthermore, although visceral fat can be measured through two-point measurements at parts with simple-shaped tissue like four limbs as described in the USP, the impedance of the abdominal portion is affected by the distribution of subcutaneous fat and internal fat, which makes it impossible to accurately measure visceral fat only thorough two-point measurement.

SUMMARY OF THE INVENTION

The present invention has been made in view of the aforementioned problems and aims to provide a body fat measuring apparatus capable of measuring visceral fat with higher accuracy than conventional body fat measuring apparatuses.

In order to attain the aforementioned object, a body fat measuring apparatus according to the present invention includes: first plural electric-current electrodes placed at positions apart from an abdominal portion of a measurement subject; first plural voltage electrodes placed on the abdominal portion of the measurement subject; second plural electric-current electrodes placed on the abdominal portion of the measurement subject such that they are spaced apart from one another by an interval sufficiently smaller than a perimeter length of the abdominal portion; second plural voltage electrodes placed on the abdominal portion of the measurement subject such that they are spaced apart from one another by an interval sufficiently smaller than the perimeter length of the abdominal portion; and a measurement control part for controlling a measuring operation of the body fat measuring apparatus. Herein, the measurement control part includes: a measurement part which causes an electric current to flow through the first electric-current electrodes and measures the impedance of a first abdominal portion from the electric-potential difference between the first voltage electrodes; a measurement part which causes an electric current to flow through the second electric-current electrodes and measures the impedance of a second abdominal portion from the electric-potential difference between the second voltage electrodes; and a body fat calculation part which calculates the body fat of the measurement subject, from the impedance of the first abdominal portion, the impedance of the second abdominal portion and characteristic values reflecting the size of the measurement subject.

In the body fat measuring apparatus according to the present invention, desirably, the first plural voltage electrodes include at least one annular-shaped electrode.

In the body fat measuring apparatus according to the present invention, desirably, the impedance of the first abdominal portion has plural measured values, and the measurement control part further includes an impedance calculation part which calculates the average of the plural measured values and sets the average value as the impedance of the first abdominal portion.

In the body fat measuring apparatus according to the present invention, desirably, the impedance of the second abdominal portion has plural measured values, and the measurement control part further includes an impedance calculation part which calculates the average of the plural measured values and sets the average value as the impedance of the second abdominal portion.

In the body fat measuring apparatus according to the present invention, preferably, the first plural electric-current electrodes are placed on four limbs.

In the body fat measuring apparatus according to the present invention, desirably, the second plural electric-current electrodes and the second plural voltage electrodes are placed at a height in the vicinity of an umbilicus position of the measurement subject.

In the body fat measuring apparatus according to the present invention, desirably, the characteristic values reflecting the size of the measurement subject include at least one of the height, the weight and the abdominal-portion perimeter length of the measuring subject.

In the body fat measuring apparatus according to the present invention, desirably, the body fat of the measurement subject includes at least one of a body fat area, a body fat volume, a subcutaneous fat area, a subcutaneous fat volume, a visceral fat area and a visceral fat volume.

The body fat measuring apparatus according to the present invention may further include a display part which displays the body fat of the measuring subject.

The foregoing and other objects, features, aspects and advantages of the present invention will become more appar-

DESCRIPTION OF THE PREFERRED EMBODIMENTS

Hereinafter, the present invention will be described in more detail with respect to embodiments thereof.

Figure 1:
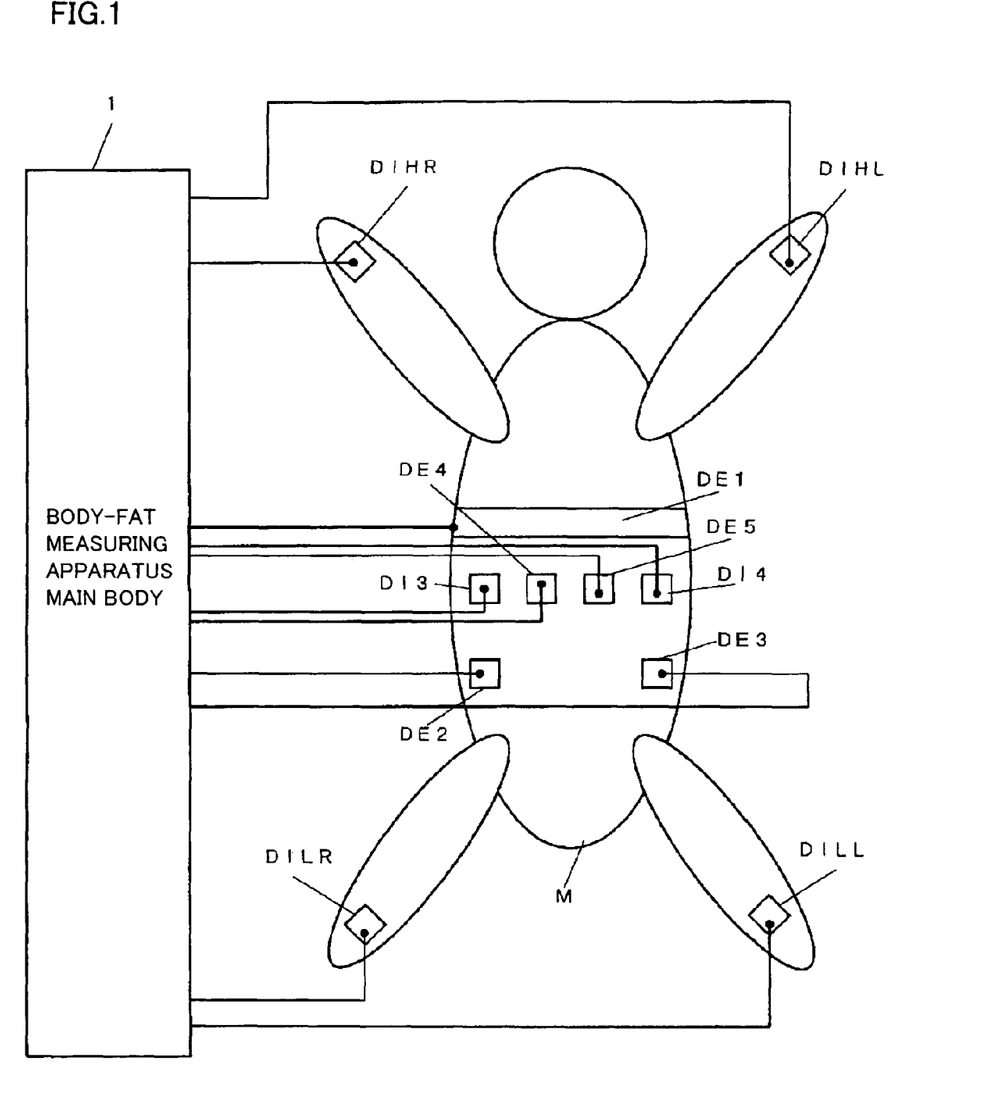
FIG. 1 illustrates a general outline of a body fat measuring apparatus according to an embodiment of the present invention.

Referring to FIG. 1, a body fat measuring apparatus according to an embodiment is configured to include a body fat measuring apparatus main body 1 and a plurality of electrodes connected to the body fat measuring apparatus main body 1. The plurality of electrodes include a right-hand electric-current electrode DIHR, a left-hand electric-current electrode DIHL, a right-leg electric-current electrode DILR, a left-leg electric-current electrode DILL, an annular-shaped voltage electrode DE1, other voltage electrodes DE2, DE3, DE4 and DE5 and other electric-current electrodes DI3 and DI4.

When the body fat measuring apparatus according to this embodiment is used for measuring visceral fat, right-hand electric-current electrode DIHR, left-hand electric-current electrode DIHL, right-leg electric-current electrode DILR, and left-leg electric-current electrode DILL are dot-shaped electrodes which are connected to the respective hands and legs distantly from an abdominal portion which is a portion to be measured. Voltage electrode DE1 is an annular-shaped electrode and is placed around a portion above the abdominal portion. Voltage electrodes DE2 and DE3 are dot-shaped electrodes and are placed at a right lumbar portion and a left lumbar portion (pit of the stomach, haunch bones) below the abdominal portion, distantly from annular-shaped voltage electrode DE1. Dot-shaped electric-current electrodes DI3 and DI4 are laterally placed along a straight line on the abdominal portion (umbilicus position) between annular-shaped voltage electrode DE1 and voltage electrodes DE2 and DE3 such that they are spaced apart by a small interval from each other to sandwich dot-shaped voltage electrodes DE4 and DE5.

Figure 2:
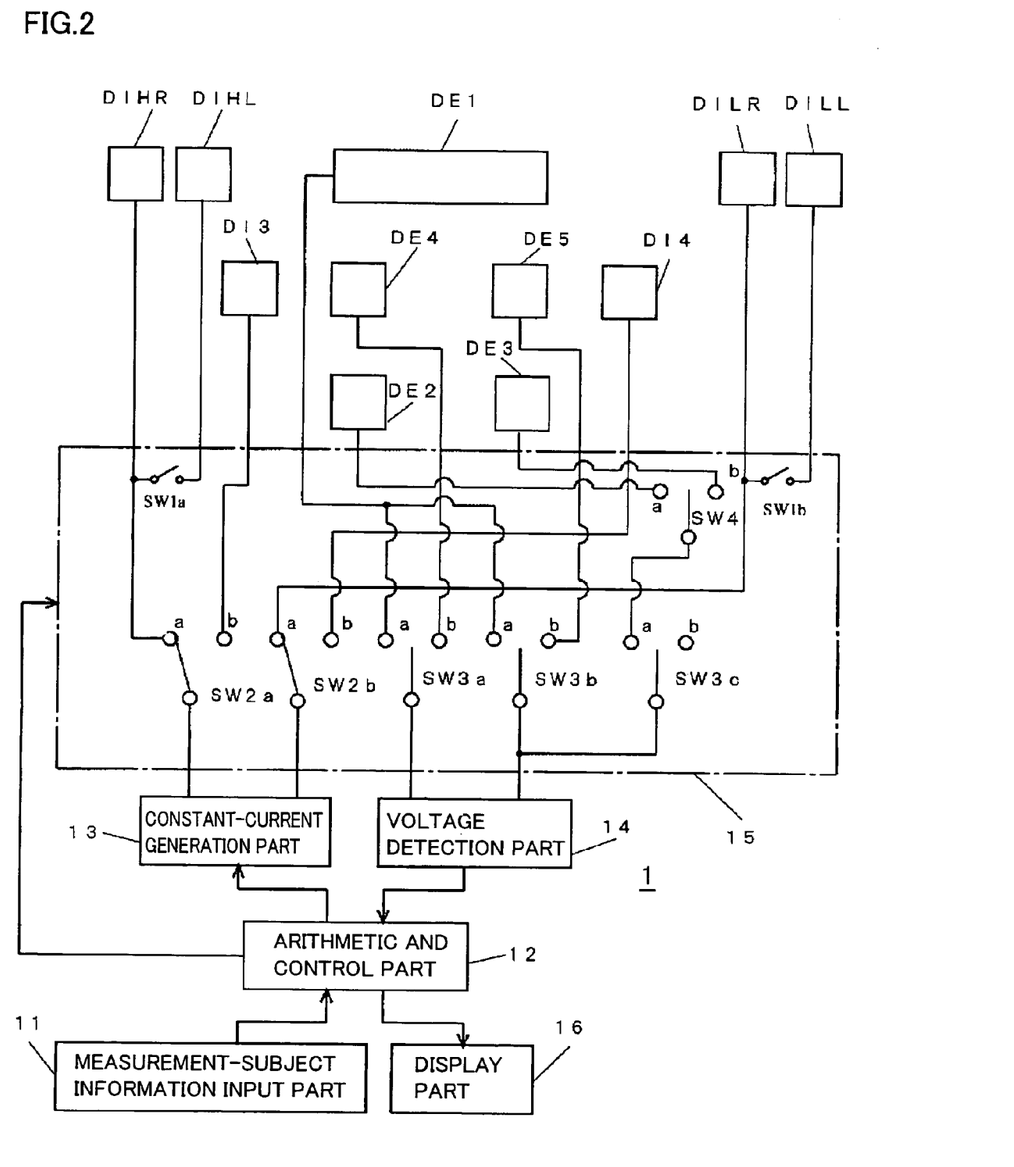
FIG. 2 is a circuit diagram illustrating a circuit structure of the body fat measuring apparatus.

Referring to FIG. 2, body fat measuring apparatus main body 1 includes a measurement-subject information input part 11, an arithmetic and control part 12, a constant-current generation part 13, a voltage detection part 14, an electrode switching part 15 and a display part 16.

Figure 3:
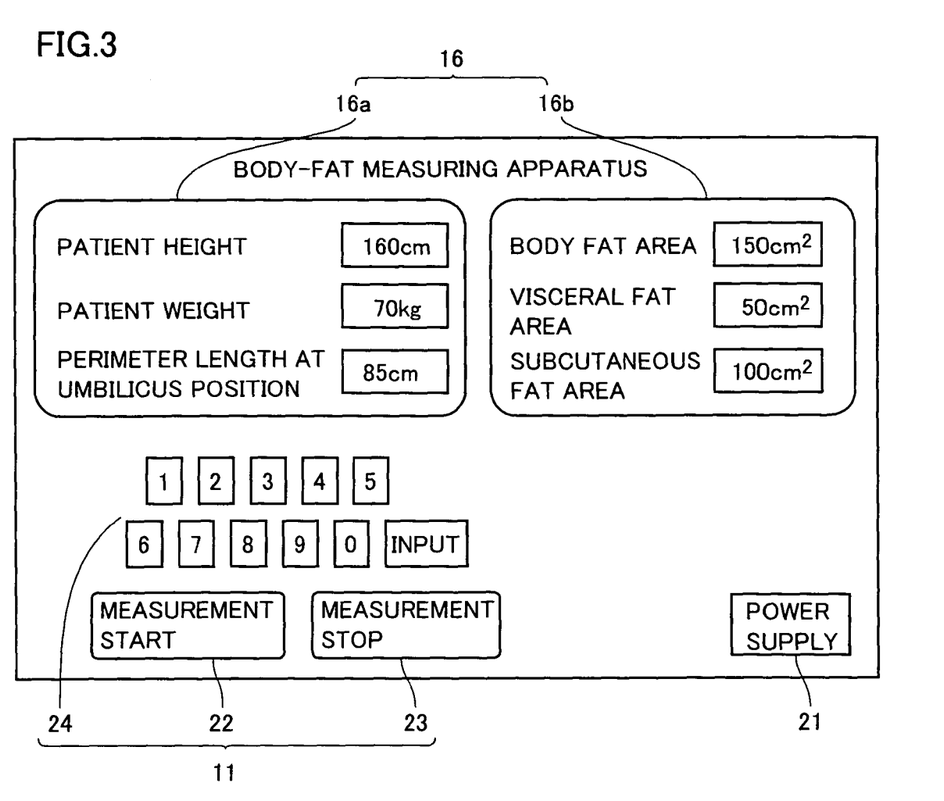
FIG. 3 illustrates an operation part and a display part of the body fat measuring apparatus.

As illustrated in FIG. 3, measurement-subject information input part 11 includes a measurement start button 22, a measurement stop button 23 and ten keys 24 which enable inputting, for example, a height, a weight and a perimeter length at the umbilicus position of the measurement subject. Arithmetic and control part 12 executes an arithmetic and controls such as switching among the electrodes, measurements of bioelectrical impedances and calculations of body fat, in accordance with incorporated programs, depending on the progress of measurements. Constant-current generation part 13 generates a high-frequency constant current to energize the living body through two electric-current electrodes. Voltage detection part 14 detects the voltage between two voltage electrodes which are placed between the two electric-current electrodes being energized. The bioelectrical impedance between the voltage electrodes can be calculated from the voltage detected by the voltage detection part 14 and the value of the constant electric-current for the energization.

Electrode switching part 15 includes a plurality of switches SW1a, SW1b, . . . and SW4 and switches, among these electrodes, the electrodes connected to constant-current generation part 13 and voltage detection part 14, under the control of arithmetic and control part 12. The common terminals of a switch SW2a and a switch SW2b are connected to one end and the other end of the output terminal of constant-current generation part 13. Further, the common terminal of a switch SW3a is connected to one end of the input of voltage detection part 14 while the common terminals of switches SW3b and SW3c are connected to the other end of the input of voltage detection part 14. Right-hand electric-current electrode DIHR is connected to an "a" terminal of switch SW2a while right-leg electric-current electrode DILR is connected to an "a" terminal of switch SW2b. Left-hand electric-current electrode DIHL is connected to right-hand electric-current electrode DIHR through switch SW1a while left-leg electric-current electrode DILL is connected to right-leg electric-current electrode DILR through switch SW1b.

Electric-current electrode DI3 and electric-current electrode DI4 are connected to a "b" terminal of switch SW2a and a "b" terminal of switch SW2b, respectively. The "a" terminals of switch SW3a and switch SW3b are connected to annular-shaped voltage electrode DE1, a "b" terminal of switch SW3a is connected to voltage electrode DE4 and a "b" terminal of switch SW3b is connected to voltage electrode DE5.

Voltage electrode DE2 is connected to an "a" terminal of switch SW3c through an "a" terminal of switch SW4, and voltage electrode DE3 is connected to the "a" terminal of switch SW3c through a "b" terminal of switch SW4. The "b" terminal of switch SW3c is opened.

Referring to FIG. 3, display part 16 includes a physique-characteristics display part 16a for displaying physique characteristics such as the height, the weight and the perimeter length at the umbilicus position of the measurement subject (patient) which have been input, and a measurement display part 16b for displaying the results of measurements such as a body fat area, a visceral fat area, and a subcutaneous fat area.

Figure 4:
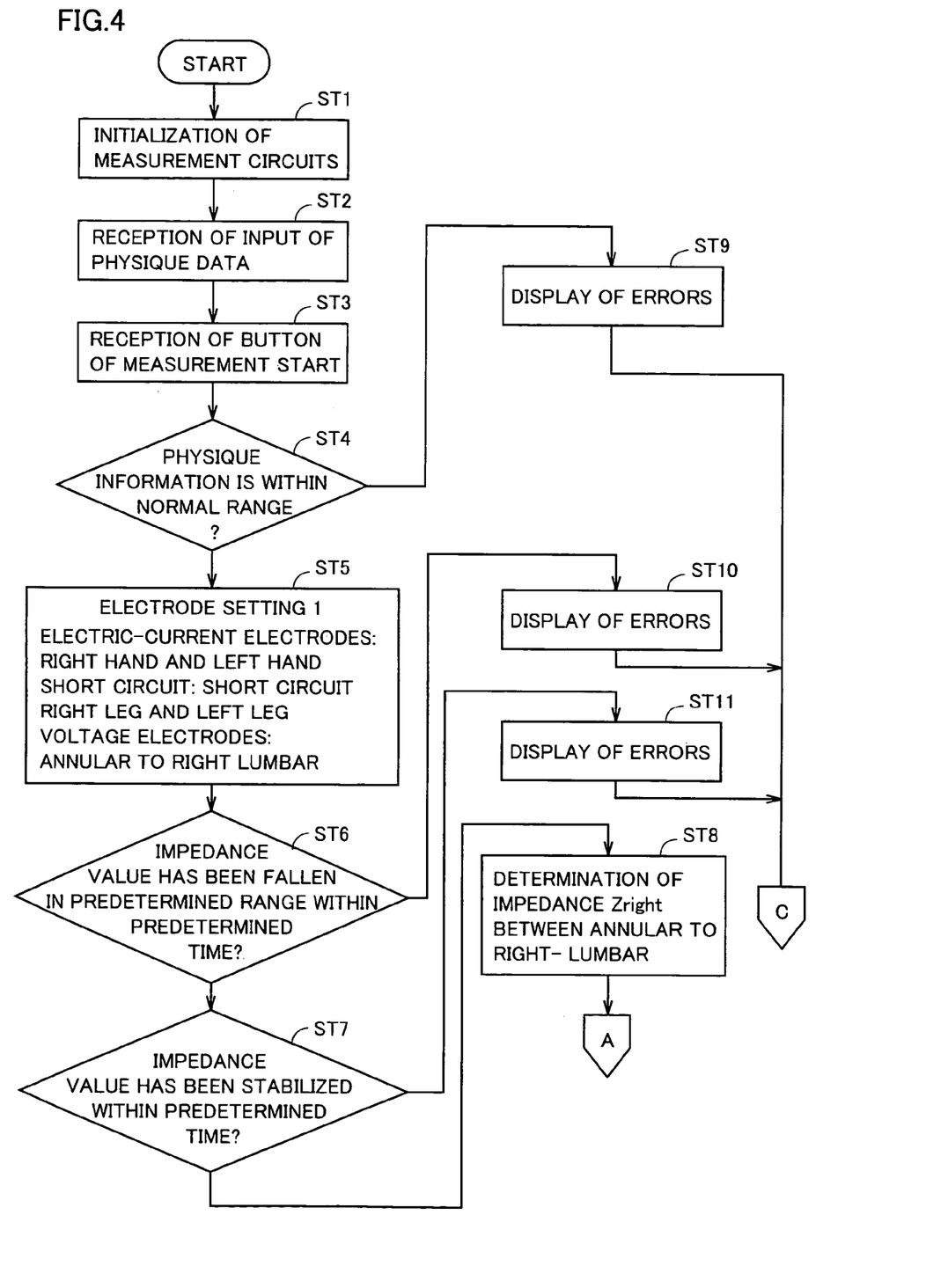
FIGS. 4 to 6 are flow charts describing a measuring process operation of the body fat measuring apparatus according to the same embodiment.
Figure 5:
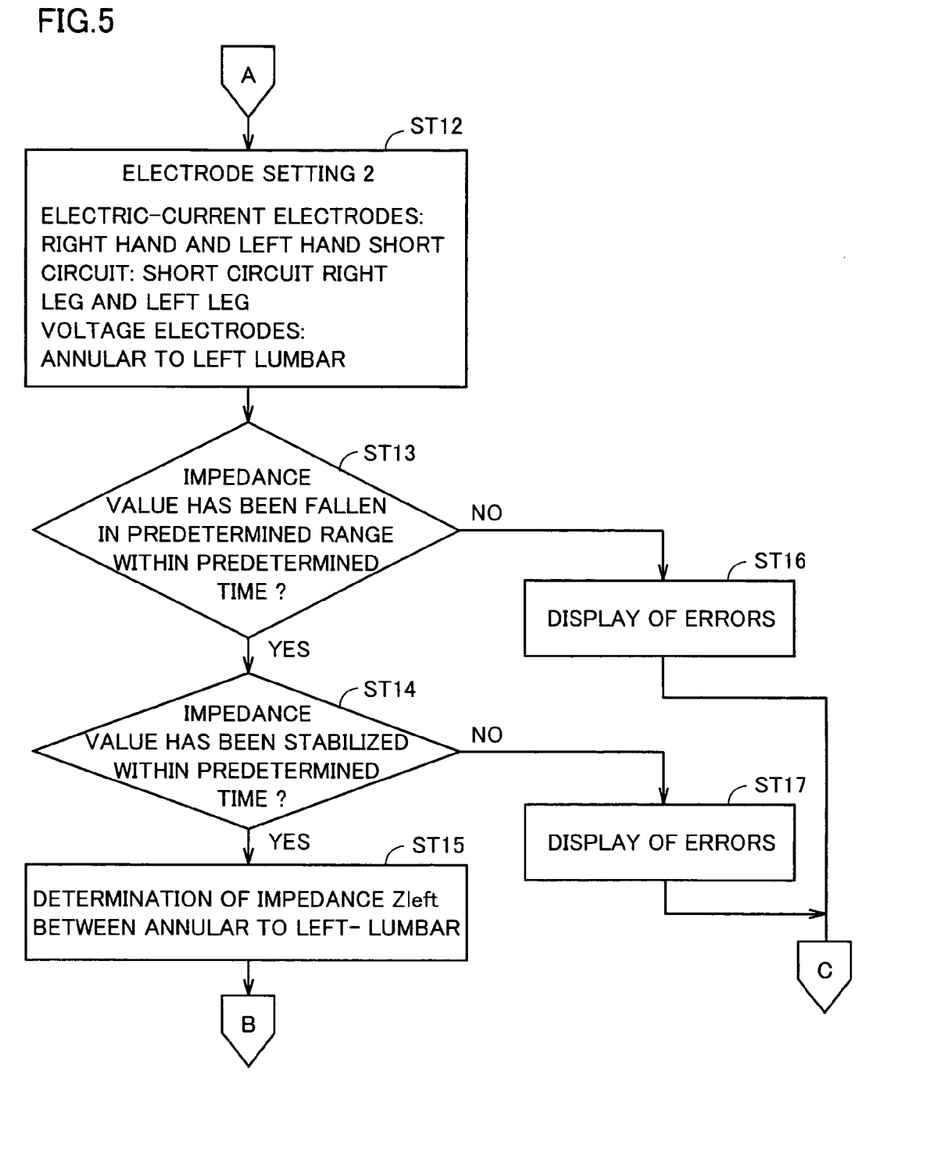
Figure 6:
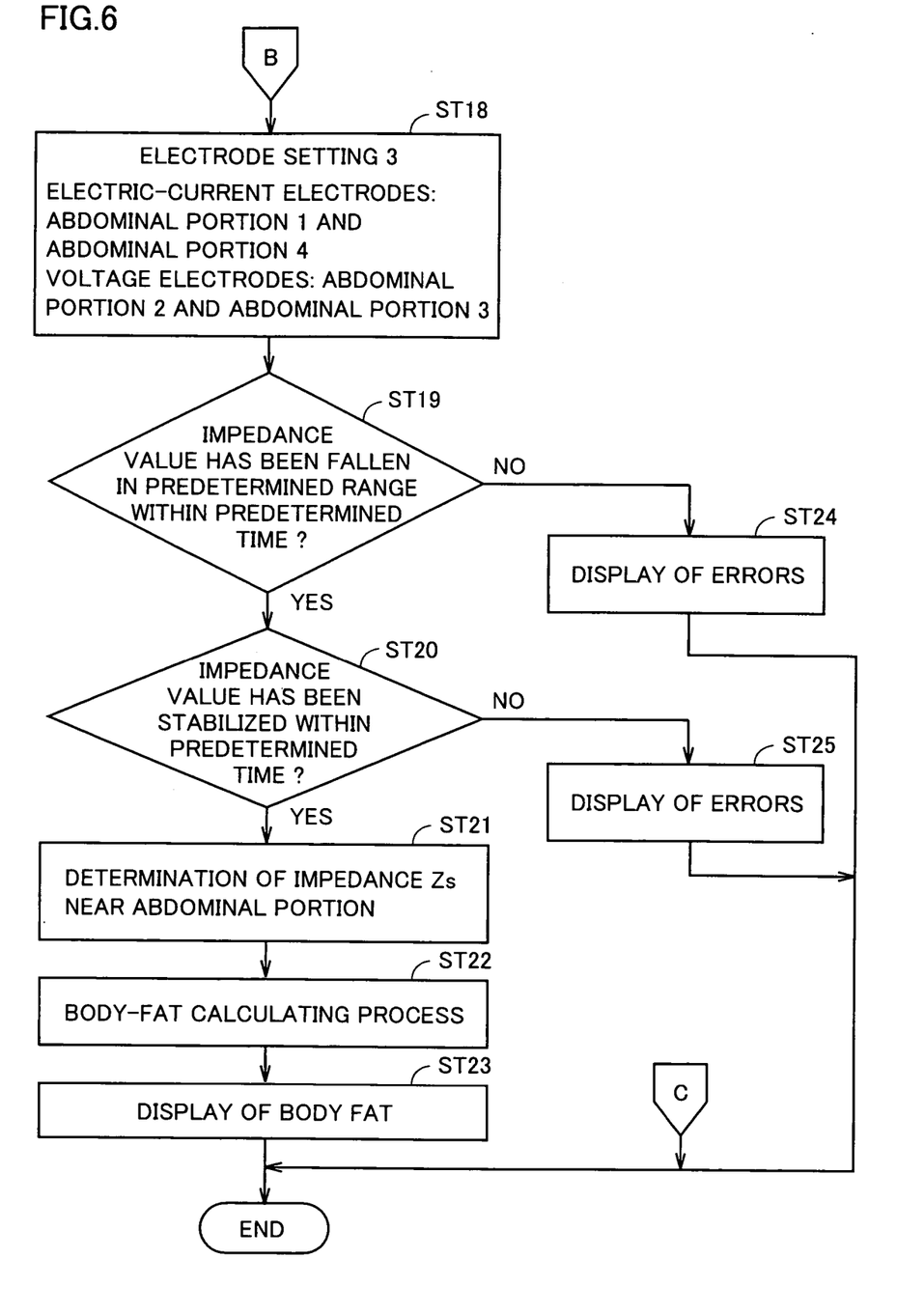

Next, there will be described a body fat measuring process executed by the body fat measuring apparatus according to this embodiment, with reference to flow charts illustrated in FIGS. 4 to 6. When a power-supply button 21 is turned on to start the operation, initialization of the measurement circuits such as clearing of a storage part in arithmetic and control part is executed in step ST1. Then, the process proceeds to step ST2. In step ST2, measurement-subject information input part 11 receives characteristic values reflecting the size of the measurement-subject body such as the weight, the height and the perimeter length at the umbilicus position and stores them in the storage part of arithmetic and control part 12. Subsequently, the process proceeds to step ST3.

In step ST3, manipulation of measurement starting button 22 performed by the measurement subject is received. Then, the process proceeds to step ST4. In step ST4, it is determined whether or not the input physique information falls within a pre-stored normal range. In the event that it does not fall within the normal range such as when it includes an extremely abnormal value, the process proceeds to step ST9 where errors are displayed. On the other hand, when it falls within the normal range, the process proceeds to step ST5.

In step ST5, a process using electrode setting 1 is executed. More specifically, switch SW1a and switch SW1b are turned on, thus short-circuiting right-hand electric-current electrode DIHR and left-hand electric-current electrode DIHL, while short-circuiting right-leg electric-current electrode DILR and left-leg electric-current electrode DILL. Further, switches SW2a, SW2b and SW3a are turned to their "a" terminals and switches SW3c and SW4 are also turned to their "a" terminals. Consequently, constant-current generation part 13 is connected between hand electric-current electrodes DIHR, DIHL and leg electric-current electrodes DILR, DILL while annular-shaped voltage electrode DE1 and right-lumbar voltage electrode DE2 are connected to voltage detection part 14. Thus, a constant electric current is flowed between hand electric-current electrodes DIHR, DIHL and leg electric-current electrodes DILR, DILL, while voltage detection part 14 detects the voltage between annular-shaped voltage electrode DE1 and right-lumber voltage electrode DE2 and a bioelectrical impedance of the abdominal portion is calculated. Next, the process proceeds to step ST6.

In step ST6, it is determined whether or not the impedance value has fallen in a predetermined range, within a predetermined time. If the impedance value has not fallen in the predetermined range within the predetermined time, it is determined that proper measurement has not been performed, and thus the process proceeds to step ST10 where errors are displayed. On the other hand, when the impedance value has fallen in the predetermined range, it is determined that proper measurement has been progressed, and the process proceeds to step ST7.

In step ST7, it is determined whether or not the impedance value has been stabilized within a predetermine time. When the impedance has not been stabilized, the process proceeds to step ST 11 where errors are displayed. On the other hand, when the impedance has been stabilized, the process proceeds to step ST8. In step ST8, the impedance Zright between annular-shaped voltage electrode DE1 and right-lumbar voltage electrode DE2 is determined and stored in the storage part of arithmetic and control part 12. Subsequently, the process proceeds to step ST12.

In step ST12, a process using electrode setting 2 is executed. More specifically, switch SW1a and switch SW1b are turned on, thus short-circuiting right-hand electric-current electrode DIHR and left-hand electric-current electrode DIHL, while short-circuiting right-leg electric-current electrode DILR and left-leg electric-current electrode DILL. Further, switches SW2a, SW2b and SW3a are turned to their "a" terminals while switch SW3c is turned to its "a" terminal and switch SW4 is turned to its "b" terminal. Consequently, constant-current generation part 13 is connected between the hand electric-current electrodes DIHR, DIHL and the leg electric-current electrodes DILR, DILL while annular-shaped voltage electrode DE1 and the left-lumbar voltage electrode DE3 are connected to voltage detection part 14. Thus, a constant electric current is flowed between hand electric-current electrodes DIHR, DIHL and leg electric-current electrodes DILR, DILL while voltage detection part 14 detects the voltage between annular-shaped voltage electrode DE1 and left-lumber voltage electrode DE3 and the bioelectrical impedance of the abdominal portion is calculated. Next, the process proceeds to step ST13.

In step ST13, it is determined whether or not the impedance value has fallen in a predetermined range, within a predetermined time. If the impedance value has not fallen in the predetermined range within the predetermined time, it is determined that proper measurement has not been performed, and the process proceeds to step ST16 where errors are displayed. On the other hand, when the impedance value has fallen in the predetermined range, it is determined that proper measurement has been progressed and the process proceeds to step ST14.

In step ST14, it is determined whether or not the impedance value has been stabilized within a predetermine time. When it has not been stabilized, the process proceeds to step ST17 where errors are displayed. On the other hand, when the impedance has been stabilized, the process proceeds to step ST15. In step ST15, an impedance Zleft between annular-shaped voltage electrode DE1 and left-lumbar voltage electrode DE3 is determined and stored in the storage part of arithmetic and control part 12. Subsequently, the process proceeds to step ST18.

In step ST18, a process using electrode setting 3 is executed. Herein, the electric-current electrodes at an abdominal portion 1 and an abdominal portion 4 and the voltage electrodes at an abdominal portion 2 and an abdominal portion 3 are selected. More specifically, switch SW2a and switch SW2b are turned to their "b" terminals while switches SW3a, SW3b and SW3c are turned to their "b" terminals. Consequently, constant-current generation part 13 is connected between electric-current electrodes DI3 and DI4 on the abdominal portion, while voltage electrodes DE4 and DE5 on the abdominal portion are connected to voltage detection part 14. Thus, a constant electric current is flowed between electric-current electrodes DI3 and DI4 on the abdominal portion while voltage detection part 14 detects the voltage between voltage electrodes DE4 and DE5 on the abdominal portion and, then, the bioelectrical subcutaneous impedance in the vicinity of the abdominal portion is calculated. Next, the process proceeds to step ST19.

In step ST19, it is determined whether or not the impedance value has fallen in a predetermined range within a predetermined time. If the impedance value has not fallen in the predetermined range within the predetermined time, it is determined that proper measurement has not been performed and the process proceeds to step ST24 where errors are displayed. On the other hand, when the impedance value has fallen in the predetermined range, it is determined that proper measurement has been progressed and, then, the process proceeds to step ST20.

In step ST20, it is determined whether or not the impedance value has been stabilized within a predetermine time. When it has not been stabilized, the process proceeds to step ST25 where errors are displayed. On the other hand, when the impedance has been stabilized, the process proceeds to step ST21. In step ST21, an impedance Zs in the vicinity of the abdominal portion is determined. Subsequently, the process proceeds to step ST22. In step ST22, the following equations are computed in an arithmetic and control part 12 to determine a visceral-fat area, a body fat area and a subcutaneous fat area.

Visceral fat area = $A*Zbody*S/L - B*Zs*R + C$

Body fat area = $D*Zbody*S/L + E$

Subcutaneous fat area = $F*Zs*R + G$ wherein

Zbody: the average of impedance Zright between the annular-shaped electrode and the right-lumbar electrode and impedance Zleft between the annular-shaped electrode and the left-lumbar electrodes R: the length of the waist S: the area of a circle having a perimeter length equal to the length of waist L: the vertical distance between the annular-shaped electrode and the left and right lumber electrodes A, B, C, D, E, F and G: coefficients Next, the process proceeds to step ST 23. In step ST23, the body fat area, the visceral fat area and the subcutaneous fat area are displayed on display part 16. FIG. 3 illustrates exemplary display. Although the body fat is determined and displayed as an area in this case, the body fat volume, the visceral-fat volume and the subcutaneous-fat volume may be determined and displayed.

Figure 7:
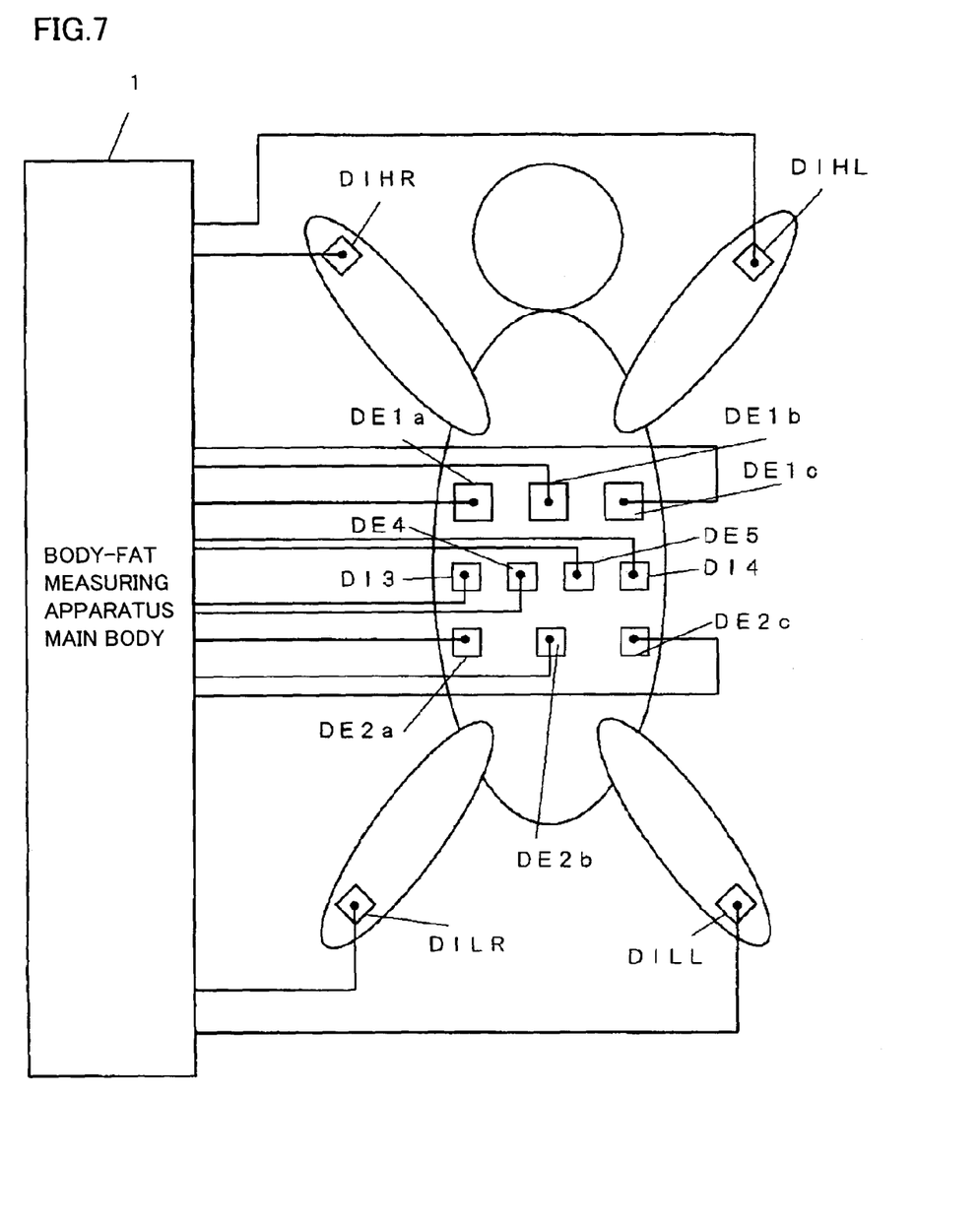
FIG. 7 illustrates a general outline of a body fat measuring apparatus according to another embodiment of the present invention.

As another embodiment of the present invention, a body fat measuring apparatus may be configured to include electrodes illustrated in FIG. 7 and employ the electrode placement illustrated therein. In this embodiment, right-hand electric-current electrode DIHR, left-hand electric-current electrode DIHL, right-leg electric-current electrode DILR and left-leg electric-current electrode DILL are similar to those of FIG. 1. Three dot-shaped voltage electrodes DE1a, DE1b and DE1c are placed at the same position as that of annular-shaped voltage electrode DE1 of FIG. 1 such that they are horizontally spaced apart from one another. Further, three voltage electrodes DE2a, DE2b and DE2c are placed at positions on the lumbar at the same height as that of the left and light lumbar voltage electrodes DE2 and DE3 of FIG. 1. Electric-current voltages DI3, DI4 and voltage electrodes DE4, DE5 placed on the abdominal portion are similar to those of FIG. 1.

With the body fat measuring apparatus according to this embodiment, a constant electric current is flowed between right-hand electric-current electrode DIHR and left-hand electric-current electrode DIHL which are being short-circuited and right-leg electric-current electrode DILR and left-leg electric-current electrode DILL which are being short-circuited. Further, the voltages between voltage electrodes DE1a and DE2a, between voltage electrodes DE1b and DE2b and between voltage electrodes DE1c and DE2c are individually detected. Thus, the respective impedances are determined and averaged and, then, the body fat area (volume) at the abdominal portion including subcutaneous fat and visceral fat is determined.

Figure 8:
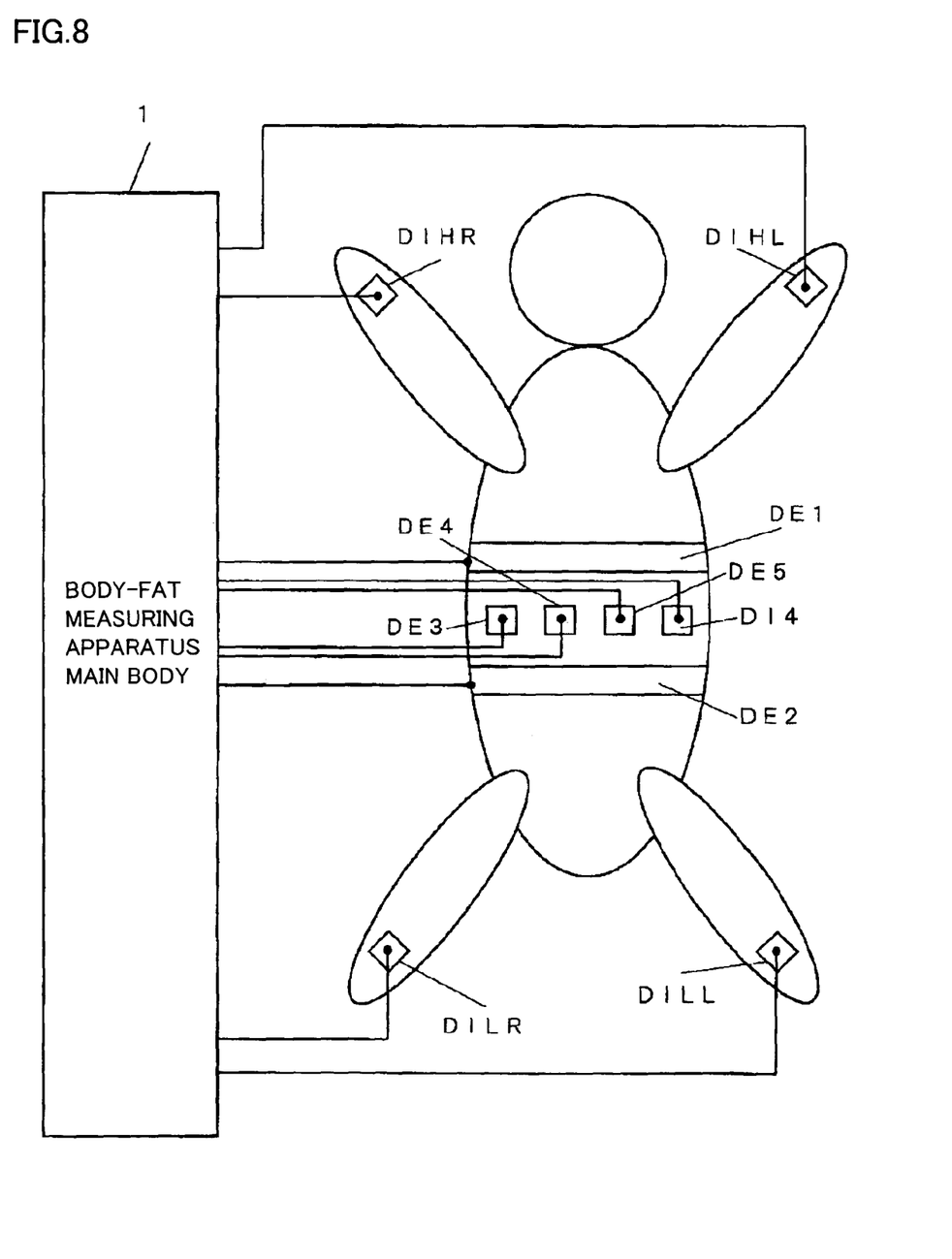
FIG. 8 illustrates a general outline of a body fat measuring apparatus according to still another embodiment of the present invention.

As still another embodiment of the present invention, a body fat measuring apparatus may be configured to include electrodes illustrated in FIG. 8 and have the electrode placement illustrated therein. In this embodiment, right-hand electric-current electrode DIHR, left-hand electric-current electrode DIHL, right-leg electric-current electrode DILR and left-leg electric-current electrode DILL are similar to those of FIG. 1. This embodiment is different from FIGS. 1 and 7 in that an annular-shaped electrode DE2 is horizontally placed at the same position as those of voltage electrode DE2 placed on the right lumbar and voltage electrode DE3 placed on the left lumbar in FIG. 1. Annular-shaped voltage electrode DE1 provided above the abdominal portion, electric-current electrodes DI3 and DI4 and voltage electrodes DE4 and DE5 which are placed on the abdominal portion are similar to those of FIG. 1.

With the body fat measuring apparatus according to this embodiment, a constant electric current is flowed between right-hand electric-current electrode DIHR and left-hand electric-current electrode DIHL which are being short-circuited and right-leg electric-current electrode DILR and left-leg electric-current electrode DILL which are being short-circuited. Then, the voltage between annular-shaped voltage electrode DE1 and annular-shaped voltage electrode DE2 is detected and the total impedance of the abdominal portion is determined. Thus, the body fat area (volume) of the abdominal portion including subcutaneous fat and visceral fat is determined.

With the present invention, electric-current electrodes for measurement of the abdominal portion are placed at positions separate from the abdominal portion and an annular-shaped voltage electrode or a plurality of voltage electrodes for measurement of the abdominal portion are placed on the abdominal portion to determine the impedance of the abdominal portion, which enables averaging the electric-potential distribution generated over the surface to suppress the variation of the electric-potential distribution due to the distribution of fat within the abdominal portion, thus enabling accurate measurement of fat in the abdominal portion. Further, electric-current electrodes and voltage electrodes for measurements in the vicinity of the abdominal subcutaneous region are placed within a sufficiently small distance to determine the impedance of only the subcutaneous fat, which enables determining the influence of the fat in the vicinity of the abdominal subcutaneous region. This enables accurately measuring visceral fat, from the impedance of the abdominal portion, the impedance of abdominal subcutaneous fat, the height, the weight and the abdominal perimeter length of the measurement subject.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A body fat measuring apparatus comprising:

first plural electric-current electrodes adapted to be placed on four limbs of a measurement subject;

first plural voltage electrodes adapted to be placed on an abdominal portion of said measurement subject;

second plural electric-current electrodes adapted to be placed on said abdominal portion of said measurement subject such that they are spaced apart from one another by an interval sufficiently smaller than a perimeter length of said abdominal portion;

second plural voltage electrodes adapted to be placed on said abdominal portion such that they are spaced apart from one another by an interval sufficiently smaller than said perimeter length of said abdominal portion; and a measurement control part for controlling a measuring operation of said body fat measuring apparatus, wherein said measurement control part includes:

a first measurement part which measures a first abdominal bioelectrical impedance of an entirety of said abdominal portion using said first plural electric-current electrodes on said four limbs and said first plural voltage electrodes on said abdominal portion, the first measurement part causing an electric current to flow through said first plural electric-current electrodes and measuring the first abdominal bioelectrical impedance from the electric-potential difference between said first plural voltage electrodes;

a second measurement part which measures a second abdominal bioelectrical impedance of a subcutaneous region of said abdominal portion using said second plural electric-current electrodes on said abdominal portion and said second plural voltage electrodes on said abdominal portion, the second measurement part causing an electric current to flow through said second plural electric-current electrodes and measuring the second abdominal bioelectrical impedance from the electric-potential difference between said second plural voltage electrodes; and a body fat calculation part which calculates an amount of visceral fat of said abdominal portion using said first abdominal bioelectrical impedance, said second abdominal bioelectrical impedance and a characteristic value reflecting the size of the measurement subject, wherein the visceral fat calculation includes subtracting a value associated with the second abdominal bioelectrical impedance from a value associated with the first abdominal bioelectrical impedance, the first abdominal bioelectrical impedance being measured using electrodes distinct from electrodes used to measure the second abdominal bioelectrical impedance.

2. The body fat measuring apparatus according to claim 1, wherein
said first plural voltage electrodes include at least one annular-shaped electrode.

3. The body fat measuring apparatus according to claim 1, wherein
said first abdominal bioelectrical impedance has plural measured values, and
said measurement control part further includes an impedance calculation part which calculates the average of said plural measured values and sets said average value as the first abdominal bioelectrical impedance.

4. The body fat measuring apparatus according to claim 1, wherein said second abdominal bioelectrical impedance has plural measured values, and said measurement control part further includes an impedance calculation part which calculates the average of said plural measured values and sets said average value as the second abdominal bioelectrical impedance.

5. The body fat measuring apparatus according to claim 1, wherein
said second plural electric-current electrodes and said second plural voltage electrodes are adapted to be placed at a height in the vicinity of an umbilicus position of said measurement subject.

6. The body fat measuring apparatus according to claim 1, wherein
said characteristic value reflecting the size of said measurement subject includes at least one of the height, the weight and the abdominal-portion perimeter length of said measuring subject.

7. The body fat measuring apparatus according to claim 1, wherein
said body fat calculation part calculates at least one of a body fat area, a body fat volume, a subcutaneous fat area, a subcutaneous fat volume, a visceral fat area and a visceral fat volume.

8. The body fat measuring apparatus according to claim 7, further comprising:
a display part which displays one or more calculations of said body fat calculation part.

* * * * *